United States Patent
Alferness

(10) Patent No.: US 7,163,507 B2
(45) Date of Patent: *Jan. 16, 2007

(54) CARDIAC REINFORCEMENT DEVICE

(75) Inventor: Clifton A. Alferness, Redmond, WA (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 348 days.

This patent is subject to a terminal disclaimer.

(21) Appl. No.: 10/668,460

(22) Filed: Sep. 23, 2003

(65) Prior Publication Data

US 2004/0059187 A1 Mar. 25, 2004

Related U.S. Application Data

(63) Continuation of application No. 10/367,346, filed on Feb. 13, 2003, now Pat. No. 6,893,392, which is a continuation of application No. 10/084,806, filed on Feb. 25, 2002, now Pat. No. 6,544,168, which is a continuation of application No. 09/696,651, filed on Oct. 25, 2000, now Pat. No. 6,375,608, which is a continuation of application No. 09/483,466, filed on Jan. 14, 2000, now Pat. No. 6,165,122, which is a continuation of application No. 08/935,723, filed on Sep. 23, 1997, now Pat. No. 6,077,218, which is a continuation of application No. 08/720,556, filed on Oct. 2, 1996, now Pat. No. 5,702,343.

(51) Int. Cl.
 *A61F 2/02* (2006.01)

(52) U.S. Cl. ....................................................... 600/37
(58) Field of Classification Search ................... 600/37

See application file for complete search history.

(56) References Cited

U.S. PATENT DOCUMENTS

| 3,983,863 A | 10/1976 | Janke et al. |
| 4,048,990 A | 9/1977 | Goetz |
| 4,403,604 A | 9/1983 | Wilkinson et al. |
| 4,428,375 A | 1/1984 | Ellman |
| 4,630,597 A | 12/1986 | Kantrowitz et al. |

(Continued)

FOREIGN PATENT DOCUMENTS

DE 3831540 4/1989

(Continued)

OTHER PUBLICATIONS

"Abstracts From the 68th Scientific Sessions, Anaheim Convention Center, Anaheim, California, Nov. 13-16, 1995", *American Heart Association Supplement to Circulation*, vol. 92, No. 8, Abstracts 1810-1813 (Oct. 15, 1995).

(Continued)

*Primary Examiner*—Scott M. Getzow
(74) *Attorney, Agent, or Firm*—Faegre & Benson LLP

(57) ABSTRACT

The present disclosure is directed to a cardiac reinforcement device (CRD) and method for the treatment of cardiomyopathy. The CRD provides for reinforcement of the walls of the heart by constraining cardiac expansion, beyond a predetermined limit, during diastolic expansion of the heart. A CRD of the invention can be applied to the epicardium of the heart to locally constrain expansion of the cardiac wall or to circumferentially constrain the cardiac wall during cardiac expansion.

16 Claims, 4 Drawing Sheets

U.S. PATENT DOCUMENTS

| | | |
|---|---|---|
| 4,690,134 A | 9/1987 | Snyders |
| 4,821,723 A | 4/1989 | Baker, Jr. et al. |
| 4,834,707 A | 5/1989 | Evans |
| 4,878,890 A | 11/1989 | Bilweis |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |
| 5,057,117 A | 10/1991 | Atweh |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,192,314 A | 3/1993 | Daskalakis |
| 5,256,132 A | 10/1993 | Snyders |
| 5,290,217 A | 3/1994 | Campos |
| 5,356,432 A | 10/1994 | Rutkow et al. |
| 5,383,840 A | 1/1995 | Heilman et al. |
| 5,385,156 A | 1/1995 | Oliva |
| 5,429,584 A | 7/1995 | Chiu |
| 5,507,779 A | 4/1996 | Altman |
| 5,524,633 A | 6/1996 | Heaven et al. |
| 5,603,337 A | 2/1997 | Jarvik |
| 5,647,380 A | 7/1997 | Campbell et al. |
| 5,702,343 A | 12/1997 | Alferness |
| 5,713,954 A | 2/1998 | Rosenberg et al. |
| 5,800,528 A | 9/1998 | Lederman et al. |
| 6,077,218 A | 6/2000 | Alferness |
| 6,126,590 A | 10/2000 | Alferness |
| 6,165,121 A | 12/2000 | Alferness |
| 6,165,122 A | 12/2000 | Alferness |
| 6,375,608 B1 | 4/2002 | Alferness |
| 6,508,756 B1 * | 1/2003 | Kung et al. ............... 600/37 |
| 6,544,168 B1 | 4/2003 | Alferness |

FOREIGN PATENT DOCUMENTS

| | | | |
|---|---|---|---|
| DE | 3831540 C | | 6/1993 |
| DE | 295 17 393 U1 | | 3/1996 |
| EP | 0 280 564 | | 8/1988 |
| GB | 2209678 | | 5/1989 |
| JP | 60203250 | | 10/1985 |
| JP | 01-145066 | | 6/1989 |
| JP | 2271829 | | 11/1990 |
| SU | 1009457 A | | 4/1983 |
| WO | WO 98/29041 | | 7/1998 |
| WO | WO 98/58598 | | 12/1998 |

OTHER PUBLICATIONS

Capomolla et al., "Dobutamine and nitroprusside infusion in patients with severe congestive heart failure: Hemodynamic improvement by discordant effects on mitral regurgitation, left atrial function, and ventricular function", *American Heart Journal*. vol. 134, No. 6, pp. 1089-1098 (Dec. 1997).

Capouya et al., "Girdling effect of Nonstimulated Cardiomyoplasty on Left Vetricular Function," *Ann. Thorac. Surg.*, 56:867-871 (1993).

Coletta et al., "Prognostic value of left ventricular volume response during dobutamine stress echocardiography", *European Heart Journal*, vol. 18, pp. 1599-1605 (Oct. 1997).

Jay N. Cohn, "The Management of Chronic Heart Failure", *The New Eng. J. of Med.*, 335 (7): 490-498 (Aug. 15, 1996).

David A. Kass et al., "Reverse Remodeling From Cardiomyoplasty in Human Heart Failure, External Constraint Versus Active Assist", *Circulation* 91 (9): 2314-2318 (May 1, 1995).

Howard R. Levin et al., "Reversal of Chronic Ventricular Dilation in Patients With End-Stage Cardiomyoplasty by Prolonged Mechanical Unloading", *Circulation* 91 (11): 2717-2720 (Jun. 1, 1995).

Oh et al., "The Effects of Prosthetic Cardiac Binding and Adynamic Cardiomyoplasty in a Model of Dilated Cardiomyopathy," *The Journal of Thoracic and Cardiovascular Surgery*, 116(1):148-153 (Jul. 1998).

Paling, "Two-Bar Fabrics (Part-Set Threading)", *Warp Knitting Technology*, Columbine Press (Publishers) Ltd., Buxton, Great Britain, p. 111 (1970).

Revista Española de Cardiologia, vol. 51, No. 7, Jul. 1998 (Abstract in English).

Abstract: Mikhail Vaynblat et al., "Cardiac Binding in Experimental Heart Failure," *Abstract in Supplement to Circulation* 92(8):1810 (Oct. 15, 1995).

* cited by examiner

CARDIAC REINFORCEMENT DEVICE

This application is a continuation of application Ser. No. 10/367,346 filed Feb. 13, 2003, now U.S. Pat. No. 6,893,392 which is a continuation of application Ser. No. 10/084,806, filed Feb. 25, 2002, issued as U.S. Pat. No. 6,544,168 on Apr. 8, 2003, which is a continuation of Ser. No. 09/696,651, filed Oct. 25, 2000, now U.S. Pat. No. 6,375,608, which is a continuation of Ser. No. 09/483,466, filed Jan. 14, 2000, now U.S. Pat. No. 6,165,122, which is a continuation of U.S. Ser. No. 08/935,723, filed Sep. 23, 1997, now U.S. Pat. No. 6,077,218, which is a continuation of U.S. Ser. No. 08/720,556, filed Oct. 2, 1996, now U.S. Pat. No. 5,702,343, which applications and issued patents are incorporated herein by reference.

BACKGROUND OF THE INVENTION

The present invention is generally directed to a device and method for reinforcement of the cardiac wall. The invention is particularly suited for the treatment of cardiac disease which result in atrial or ventricular dilation. The invention provides reinforcement of the cardiac wall during diastolic chamber filling to prevent or reduce cardiac dilation in patients known to have experienced such dilation or who have a predisposition for such dilation occurring in the future. The cardiac reinforcement structure is typically applied to the epicardial surface of the heart.

Cardiac dilation occurs with different forms of cardiac disease, including heart failure. In some cases, such as post-myocardial infarction, the dilation may be localized to only a portion of the heart. In other cases, such as hypertrophic cardiomyopathy, there is typically increased resistance to filling of the left ventricle with concomitant dilation of the left atria. In dilated cardiomyopathy, the dilation is typically of the left ventricle with resultant failure of the heart as a pump. In advanced cases, dilated cardiomyopathy involves the majority of the heart.

With each type of cardiac dilation, there are associated problems ranging from arrhythmias which arise due to the stretch of myocardial cells, to leakage of the cardiac valves due to enlargement of the valvular annulus. Devices to prevent or reduce dilation and thereby reduce the consequences of dilation have not been described. Patches made from low porosity materials, for example Dacron™, have been used to repair cardiac ruptures and septal defects, but the use of patches to support the cardiac wall where no penetrating lesion is present has not been described.

Drugs are sometimes employed to assist in treating problems associated with cardiac dilation. For example, digoxin increases the contractility of the cardiac muscle and thereby causes enhanced emptying of the dilated cardiac chambers. On the other hand, some drugs, for example, beta-blocking drugs, decrease the contractility of the heart and thus increase the likelihood of dilation. Other drugs including angiotensin-converting enzyme inhibitors such as enalopril help to reduce the tendency of the heart to dilate under the increased diastolic pressure experienced when the contractility of the heart muscle decreases. Many of these drugs, however, have side effects which make them undesirable for long-term use.

Accordingly, there is a need for a device that can reduce or prevent cardiac dilation and reduce the problems associated with such dilation.

SUMMARY OF THE INVENTION

The present invention is directed to a device and method for reinforcement of the cardiac wall. According to the invention, a cardiac reinforcement device includes a biomedical material which can be applied to the epicardial surface of the heart and which expands to a predetermined size that is selected to constrain cardiac expansion beyond a predetermined limit. A biomedical material suitable for a cardiac reinforcement device can be an elastic or non-elastic mesh or non-mesh material.

In one embodiment, a cardiac reinforcement device is a biomedical material in the form of a patch. The size of the patch is selected to locally constrain cardiac expansion.

In another embodiment, a cardiac reinforcement device is a biomedical material shaped as a jacket with a predetermined size selected for the jacket to surround the epicardial surface of the heart and circumferentially constrain cardiac expansion. In one embodiment, a cardiac reinforcement jacket may be applied to the epicardial surface via a minimally invasive procedure such as thorascopy.

A cardiac reinforcement jacket can include a securing arrangement for securing the jacket to the epicardial surface of the heart. The cardiac reinforcement jacket can also include a mechanism for selectively adjusting the predetermined size of the jacket around the epicardial surface of the heart. The adjustment mechanism can include a slot having opposing lateral edges which when pulled together decrease the volumetric size of the jacket. In an alternative embodiment, a selective size adjustment mechanism can include an inflatable member mounted between the jacket and the epicardial surface of the heart. Inflation of the inflatable member provides for reduction in the volumetric size of the jacket.

A cardiac reinforcement device of the invention can be used to treat cardiomyopathy or to reduce the diastolic volume of the heart.

DETAILED DESCRIPTION

Figure 1:
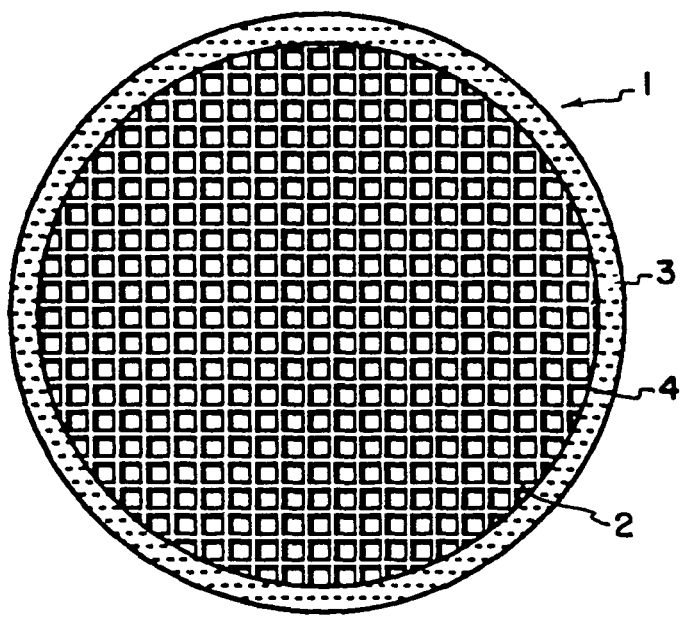
FIG. 1 is a frontal view of one embodiment of a cardiac reinforcement patch.

The present invention is directed to reinforcement of the heart wall during diastolic filling of a chamber of the heart. The invention is particularly suited for use in cardiomyopathies where abnormal dilation of one or more chambers of the heart is a component of the disease.

As used herein, "cardiac chamber" refers to the left or right atrium or the left or right ventricle. The term "myocardium" refers to the cardiac muscle comprising the contractile walls of the heart. The term "endocardial surface" refers to the inner walls of the heart. The term "epicardial surface" refers to the outer walls of the heart.

The heart is enclosed within a double walled sac known as the pericardium. The inner layer of the pericardial sac is the visceral pericardium or epicardium. The outer layer of the pericardial sac is the parietal pericardium.

According to the present invention, a cardiac reinforcement device (CRD) limits the outward expansion of the heart wall during diastolic chamber filling beyond a predetermined size. The expansion constraint applied to the heart by a CRD is predetermined by the physician based on, for example, cardiac output performance or cardiac volume. In contrast to known ventricular assist devices which provide cardiac assistance during systole, a CRD according to the present disclosure provides cardiac reinforcement during diastole.

A CRD is made from a biomedical material which can be applied to the epicardial surface of the heart. As used herein, a "biomedical material" is a material which is physiologically inert to avoid rejection or other negative inflammatory response. A CRD can be prepared from an elastic or substantially non-elastic biomedical material. The biomedical material can be inflexible, but is preferably sufficiently flexible to move with the expansion and contraction of the heart without impairing systolic function. The biomedical material should, however, constrain cardiac expansion, during diastolic filling of the heart, to a predetermined size. Examples of suitable biomedical materials include perforate and non-perforate materials. Perforate materials include, for example, a mesh such as a polypropylene or polyester mesh. Non-perforate materials include, for example, silicone rubber.

A biomedical material suitable for a device of the invention generally has a lower compliance than the heart wall. Even though the biomedical material is less compliant than the heart wall, some limited expansion of an elastic biomedical material can occur during cardiac filling.

In an alternative embodiment, the biomedical material can be substantially non-elastic. According to this embodiment, the term "substantially non-elastic" refers to a material which constrains cardiac expansion during diastole at a predetermined size, but which has substantially no elastic properties.

Regardless if the biomedical material is elastic or non-elastic, advantageous to a CRD according to the present disclosure is cardiac reinforcement which is provided during diastole. Moreover, a CRD as disclosed herein does not provide cardiac assistance through active pumping of the heart.

I. CRD Patch

In one embodiment, a cardiac reinforcement device (CRD) provides for local constraint of the heart wall during cardiac expansion. According to this embodiment, a CRD is a "patch" that provides reinforcement of the heart wall at a localized area, such as a cardiac aneurysm or at an area of the myocardium which has been damaged due to myocardial infarction. When discussing a "patch", "predetermined size" of the patch means that the size of the patch is selected to cover an area of the epicardial surface of the heart in need of reinforcement without completely surrounding the circumference of the heart.

A CRD patch can be prepared from the biomedical materials described above. In a preferred embodiment, the patch is an open mesh material.

A CRD patch can be applied to the epicardial surface of the heart over or under the parietal pericardium. A patch is typically applied to the epicardial surface by suturing around the periphery of the patch. The peripheral edge of the patch can include a thickened "ring" or other reinforcement to enhance the strength of the patch at the point of suture attachment to the epicardium. Generally, a patch is applied to the epicardium through a thoracotomy or other incision providing sufficient exposure of the heart.

II. CRD Jacket

In another embodiment, a CRD is a jacket that circumferentially surrounds the epicardial surface of the heart. When applied to the heart, a CRD jacket can be placed over or under the parietal pericardium.

A CRD applied to the epicardium is fitted to a "predetermined size" for limitation of cardiac expansion. According to a jacket embodiment, "predetermined size" refers to the predetermined expansion limit of the jacket which circumferentially constrains cardiac expansion during diastolic filling of the heart. In practice, for example, a physician could measure cardiac output and adjust the jacket size to an optimal size for the desired effect. In this example, the optimal size is the "predetermined size". In one embodiment, the predetermined size can be adjusted for size reduction as the cardiac size is reduced.

In one embodiment, the CRD jacket is a cone-shaped tube, having a base broader than the apex, which generally conforms to the external geometry of the heart. When applied to the epicardial surface of the heart, the base of the jacket is oriented towards the base of the heart, and the apex of the jacket is oriented towards the apex of the heart. Typically, the base of the jacket includes an opening for applying the jacket by passing the jacket over the epicardial surface of the heart. The apical end of the jacket can be a continuous surface which covers the apex of the heart. Alternatively, the apex of the jacket can have an opening through which the apex of the heart protrudes.

A cardiac reinforcement jacket, as disclosed herein, is not an inflatable device that surrounds the heart. Rather, the device is typically a single layer of biomedical material. In one embodiment discussed below, an inflatable member can be included with the device, but the inflatable member serves to reduce the volume within a localized region of the jacket and does not follow the entire jacket to surround the epicardial surface of the heart.

In one embodiment, the CRD jacket can be secured to the epicardium by a securing arrangement mounted at the base of the jacket. A suitable securing arrangement includes, for example, a circumferential attachment device, such as a cord, suture, band, adhesive or shape memory element which passes around the circumference of the base of the jacket. The ends of the attachment device can be fastened together to secure the jacket in place. Alternatively, the base of the jacket can be reinforced for suturing the base of the jacket to the epicardium.

Various sized CRD jackets can be prepared such that different sized jackets are used for different predetermined cardiac expansion sizes or expansion ranges. Alternatively, a CRD jacket can include a mechanism for selectively adjusting the size of the jacket. A mechanism for selectively adjusting the volumetric size of the jacket theoretically provides for a "one size fits all" device. More importantly, however, an adjustable jacket provides the ability to titrate (readjust) the amount of cardiac reinforcement by graded reduction in jacket size as therapeutic reduction of cardiac expansion occurs.

A mechanism for selectively adjusting the size of the jacket can include a slot which opens at the base of the jacket and extends toward the apex end of the CRD. If the apex end of the CRD jacket is open, the apical extent of the slot can be continuous with the apex opening. The slot includes opposing lateral edges. By adjusting the proximity of the opposing lateral edges, the overall size of the jacket can be varied. Moving the opposing edges of the slot closer together narrows the slot and reduces the volumetric size of the jacket. The opposing edges of the slot can be fastened together at a predetermined proximity by, for example, one or more lateral attachment devices, such as a cord, suture, band, adhesive or shape memory element attached to each lateral edge.

In another embodiment, a mechanism for selectively adjusting the size of the jacket can be an inflatable member. According to this embodiment, the inflatable member is mounted between the jacket and the epicardium. The volumetric size of the jacket can be reduced by inflating the inflatable member through an inflation port with, for example, a gas or liquid. As cardiac expansion volume responds to cardiac constraint by size reduction, the predetermined size of the jacket can then be reduced by inflating the inflatable member within the jacket. Once inflated, the size of the inflatable member is preferably maintained until therapeutic response causes a need for further inflation. According to the invention, the inflation of the inflatable member provides a reduction in the predetermined size of the jacket by a fixed increase in volume of the inflatable member. The inflatable member is not rhythmically inflated and deflated to provide assistance to cardiac contraction during systole.

The biomedical material of the invention can be radioluscent or radiopaque. In one embodiment, the material of the jacket can be made radiopaque by inclusion of radiopaque markers for identification of the outside surface of the heart, the expansion slot or inflation port. As used herein, radiopaque means causing the CRD to be visible on x-ray or fluoroscopic viewing. Suitable radiopaque markers include, for example, platinum wires, titanium wires and stainless steel wires.

A CRD according to the present disclosure provides a new method for the treatment of cardiac disease. As used herein, cardiac disease includes diseases in which dilation of one of the chambers of the heart is a component of the disease. Examples include heart failure or cardiomyopathy. Heart failure can occur as a result of cardiac dilation due to ventricular hypertrophy or secondary to, for example, valvular incompetency, valvular insufficiency or valvular stenosis. Cardiomyopathy, according to the invention, can be primary or secondary to infection, ischemia, metabolic disease, genetic disorders, etc.

It is foreseen that constraint of cardiac expansion by a device of the invention can provide reduced cardiac dilation. Reduced cardiac dilation can cause reduction in the problems associated with cardiac dilation such as arrhythmias and valvular leakage. As reduction of cardiac dilation occurs, selective reduction of the predetermined size of the jacket also provides continued reinforcement for the size reduced heart.

A CRD jacket can also be used to measure cardiac performance. According to this embodiment, the CRD jacket is rendered radiopaque by use of a radiographic marker. The radiographic markers are distributed throughout the jacket over the surface of the heart. By evaluation of the markers relative to one another with each heart beat, cardiac performance may be measured. As such, evaluation of cardiac performance may assist in adjusting the predetermined size of a CRD jacket.

A CRD as described herein can be applied to the epicardium of a heart through a thoracotomy or through a minimally invasive procedure. For a minimally invasive procedure a CRD placement tool can be used to apply the CRD over the epicardium of the heart through a thorascopic incision. According to this embodiment, a CRD placement tool includes a cannula, a stiff rod or wire and a guide tube. For placement of a CRD, the wire is threaded through the guide tube which is passed around the circumference of the base of the jacket. The CRD with wire and guide tube passed through the base opening are then passed into the cannula. The cannula is of sufficient length and diameter to enclose the CRD, wire and guide tube during passage of the placement tool through a thorascopic incision. The placement tool is passed into the thoracic cavity and positioned at a point near the apex of the heart. When in position, the wire and guide tube are pushed out of the cannula away from the operator. Once outside the cannula, the wire and guide tube sufficiently expand the opening of the base of the CRD jacket to pass over the epicardial surface of the heart. When the CRD jacket is in position over the epicardial surface, the wire, guide tube and cannula can be removed. A second incision can then be made to provide access for suitable surgical instruments to secure or adjust the size of the CRD.

The invention will now be further described by reference to the drawings.

FIG. 1 is a frontal view of one embodiment of a cardiac reinforcement patch 1. The CRD patch 1 shown here is a mesh biomedical material 2 having a thickened peripheral ring 3 which reinforces the peripheral edge 4 of the patch for attachment of the patch to the epicardial surface of the heart.

Figure 2:
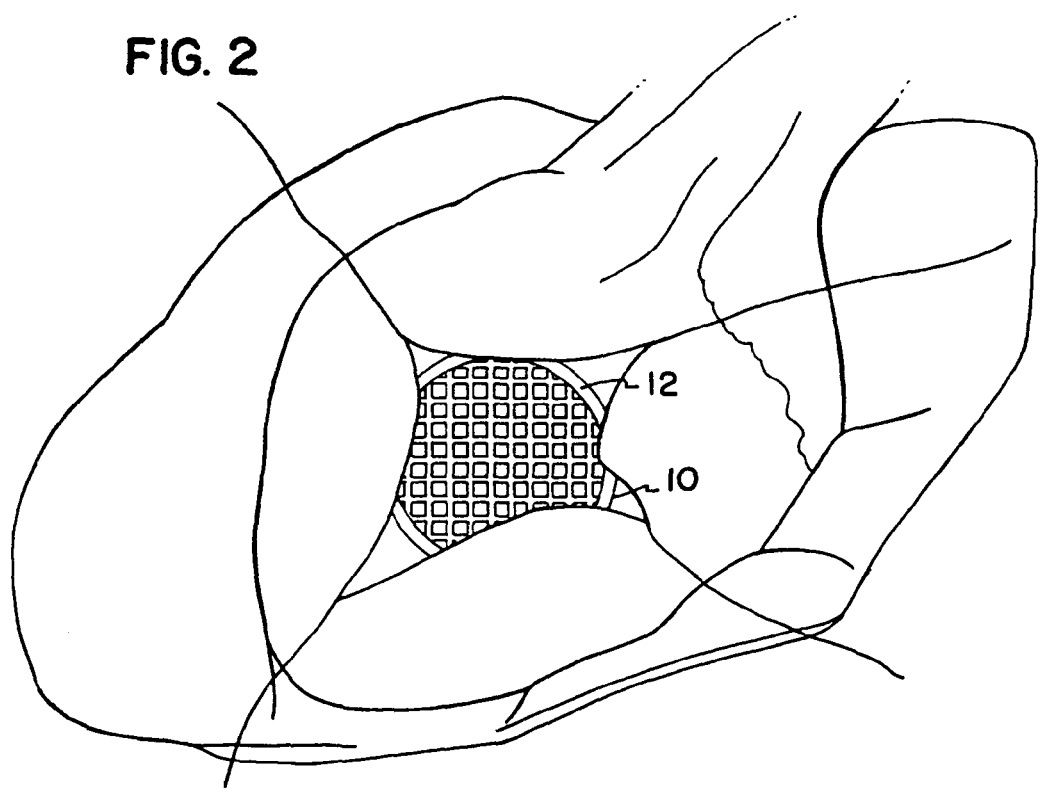
FIG. 2 is a perspective view of the cardiac reinforcement patch of FIG. 1 in place on the epicardium of a heart.

FIG. 2. is a perspective view of a CRD patch 10 in place on the epicardial surface of a heart 11, for example, over a cardiac aneurysm (not shown) of the heart. In one preferred embodiment, the patch 10 is sized to cover the extent of the cardiac aneurysm and is placed on the epicardial surface of the heart 11. In practice, the thorax is surgically opened and the region of the heart 11 with the aneurysm (not shown) is located and exposed. The patch 10 is placed over the aneurysm and sutured in place around the periphery 12 of the patch to provide sufficient constraint to prevent further dilation of the aneurysm.

Figure 3:
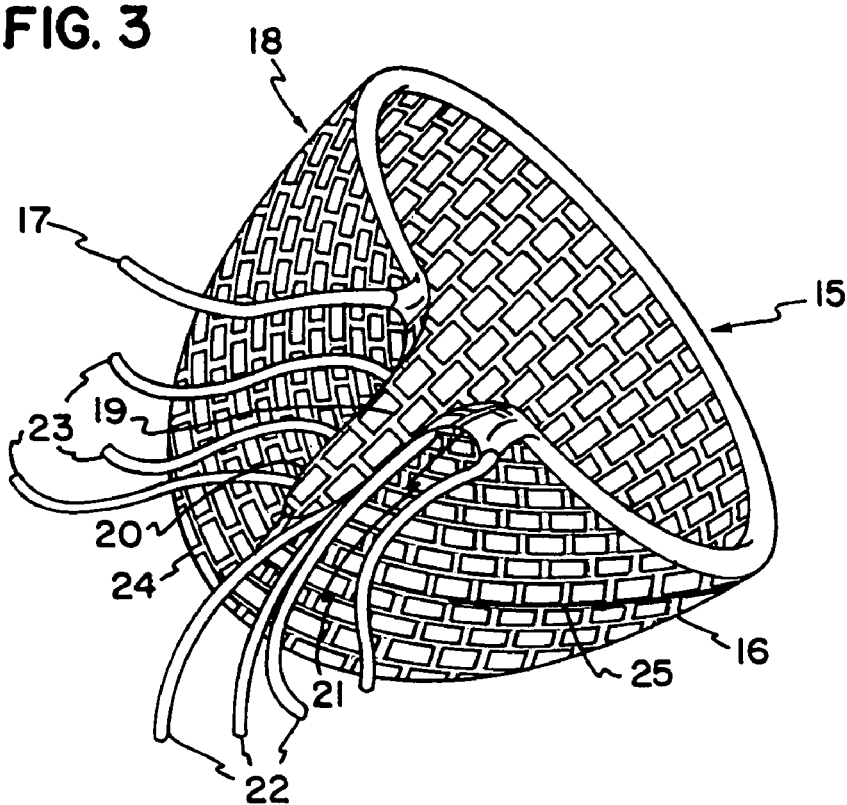
FIG. 3 is a perspective view of one embodiment of a cardiac reinforcement jacket according to the invention.

FIG. 3 is a perspective view of one embodiment of a CRD jacket 15 according to the invention. According to the embodiment shown, the jacket 15 is a mesh material 16, and includes a circumferential attachment device 17 at the base end 18 of the CRD jacket. The apex end 24 of the jacket 15 is closed. The jacket 15 shown also includes a slot 19 having opposing lateral edges 20 and 21, and fasteners (e.g. lateral attachment device 22 and 23) for selectively adjusting the volumetric size of the jacket 15. The CRD jacket 15 shown also includes radiopaque markers 25 for visualizing the surface of the heart through radiographic study.

Figure 4:
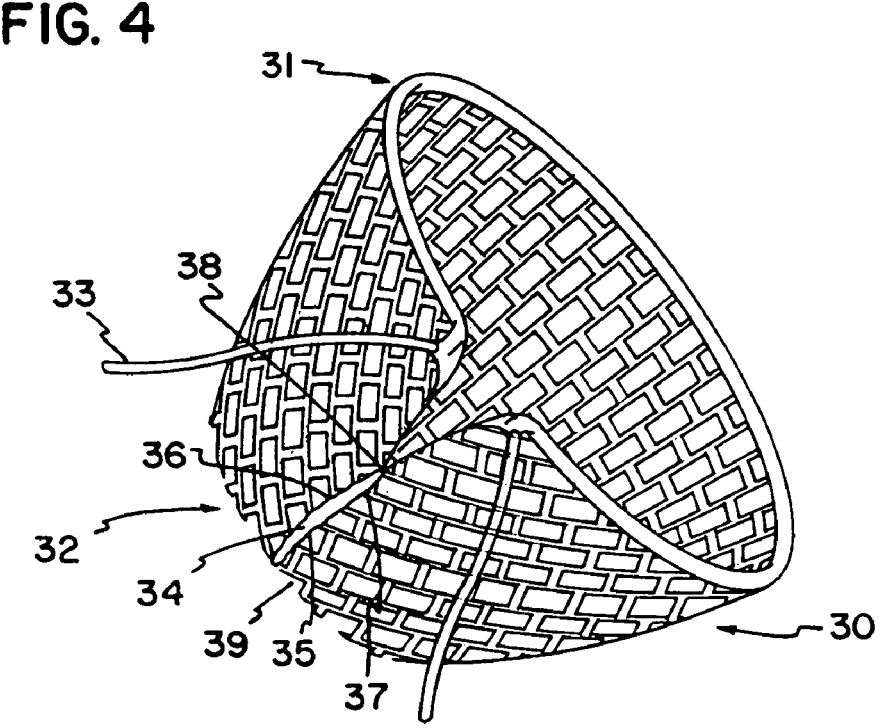
FIG. 4 is a second embodiment of a cardiac reinforcement jacket according to the invention.

FIG. 4 is an alternative embodiment of a CRD jacket 30. Similar to the embodiment shown in FIG. 3, the embodiment of FIG. 4 includes a base end 31 and an apex 32 end. The base end includes a circumferential attachment device 33 for securing the CRD jacket 30 to the heart. The CRD jacket 30 of FIG. 4 also includes a slot 34 having opposing lateral edges 35, 36. The lateral edges 35, 36 are shown pulled together at 37 by a lateral attachment device 38, for example, a suture. In contrast to the embodiment shown in FIG. 3, the embodiment shown in FIG. 4 has an opening 39 at the apex end 32 of the CRD jacket 30.

Figure 5:
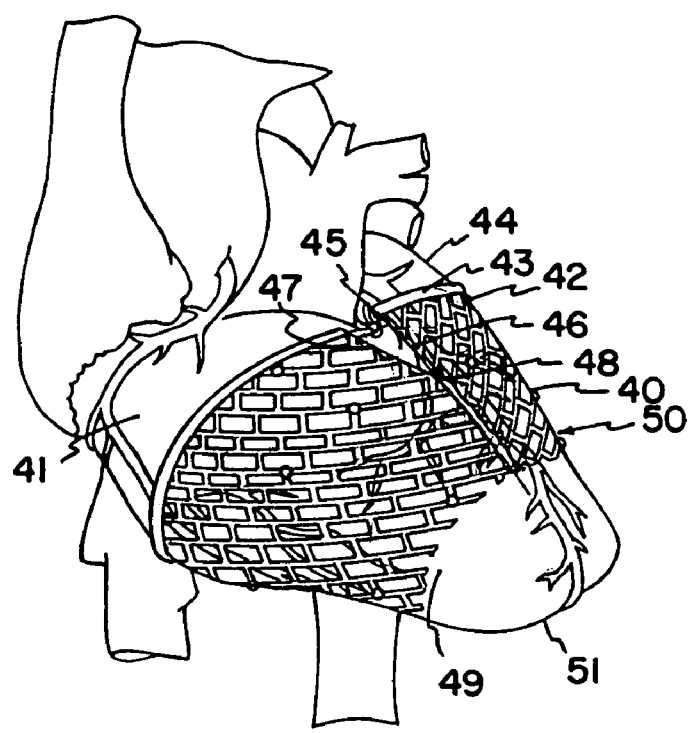
FIG. 5 is a perspective view of the embodiment of the cardiac reinforcement jacket shown in FIG. 3 in place around the heart.

FIG. 5. is a perspective view of a CRD jacket 40 around a heart 41. According to the embodiment shown, at the base 42 of the jacket 40, there is a circumferential attachment device 43 which secures the CRD jacket 40 near the base of the heart 44. A slot 45, is shown with opposing lateral edges 46, 47 fastened together by a lateral attachment device 48. In the embodiment shown, the CRD jacket 40 has an opening 49 at the apical end 50 of the jacket. The apex of the heart 51 protrudes through the opening 49 at the apical end 50 of the jacket 40.

Still referring to FIG. 5, in a preferred embodiment, if one or more of the lateral attachment device 48 are made of an elastic material, such as silicone rubber, the device can provide a way of applying a graded constraint around the outside of the heart 41 to reduce cardiac dilation over time. In practice, the jacket would be placed over the heart 41 as shown, either over or under the parietal pericardium (not shown). The circumferential attachment device 43 and lateral attachment device 48 would then be tightened to cause a constraining effect on the outside of the heart.

In a preferred embodiment, if one or more of the lateral attachment cords 48 is made of an elastic material, such as silicone rubber, surface pressure exerted on the epicardial surface of the heart varies as a function of the amount of dilation of the heart. This variable pressure has the effect of reducing the cardiac dilation to a certain point and then stopping because the surface pressure drops to a negligible amount. The amount of constraint or reduction in dilation that is accomplished over time and the resultant cardiac performance may be monitored radiographically using techniques known in the art, for example fluoroscopy, by observing radiographic markers (FIG. 4, 25), if present.

Figure 6:
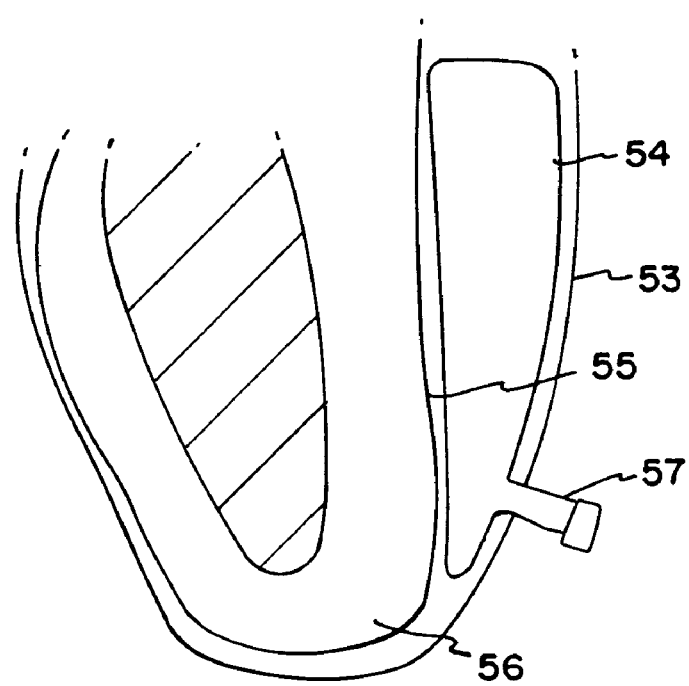
FIG. 6 is a schematic cross sectional view of one embodiment of a mechanism for selectively adjusting the predetermined size of a cardiac reinforcement jacket.

FIG. 6 is a schematic cross sectional view of an alternative embodiment of an arrangement for selectively adjusting the predetermined size of a jacket 53. According to this embodiment, an inflatable member 54 is inserted within the jacket 53 between the jacket 53 and the epicardial surface 55 of the heart 56. The inflatable member 54 includes a filling apparatus 57 for entry of a fluid (liquid or gas) to inflate the inflatable member 54 and reduce the predetermined size of the jacket 53.

Figure 7:
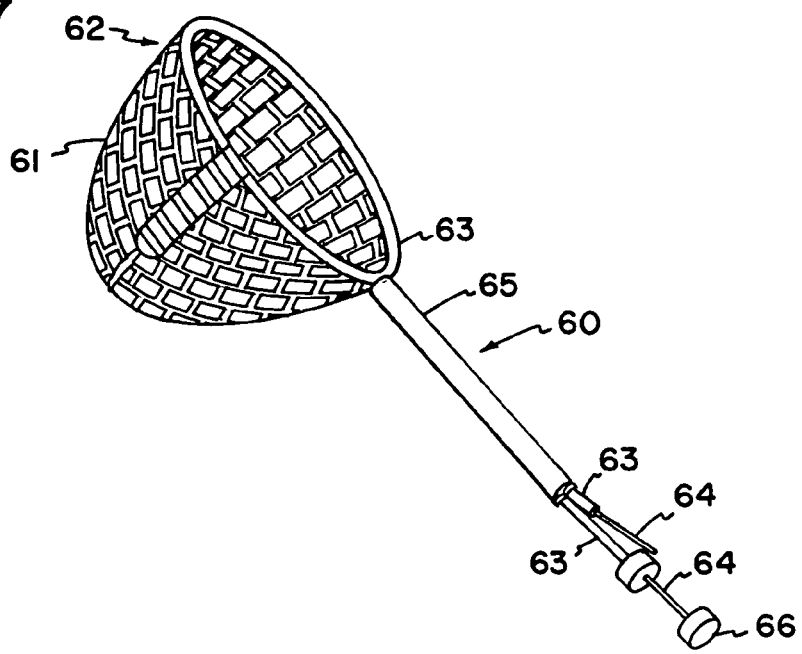
FIG. 7 is a perspective view of a placement tool which can be used for applying a cardiac reinforcement jacket.

FIG. 7 is a perspective view of a placement tool 60 which can be used for placement of a CRD jacket 61 around the epicardium of the heart. As shown here, the base end of the jacket 62 is held open by guide tube 63 through which is passed a wire or stiffening rod 64. The wire 64 can be removed from the guide tube 63 by pulling on the wire extraction grip 66. The placement tool 60 includes a cannula 65 which encloses the jacket 61, guide tube 63 and wire 64 during insertion of the tool into a thorascopic incision.

Figure 8:
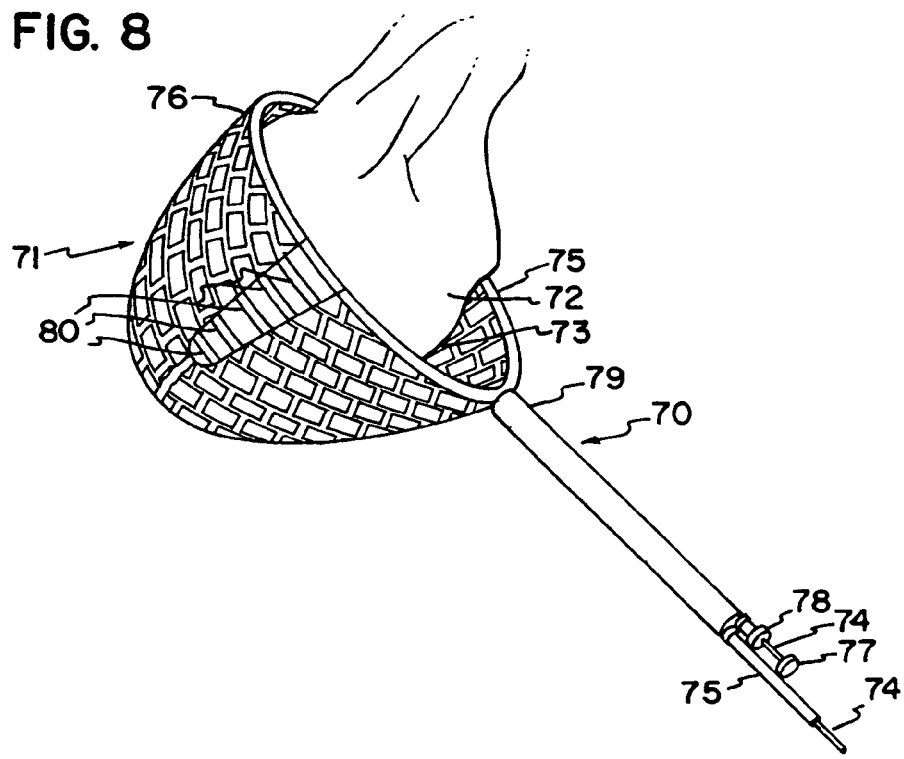
FIG. 8 is a perspective view of a placement tool being employed to place a cardiac reinforcement jacket over the heart.

FIG. 8 is a perspective view of a placement tool 70 being employed to place a jacket 71 over the heart 72 on the outside of the parietal pericardium 73. The placement tool 70 is guided through a small incision in the thorax and the jacket 71 is maneuvered into position over the heart 72. Once the jacket 71 is in proper position, the wire 74, which is passed through the guide tube 75 around the base 76 of the jacket 71, is extracted from the guide tube 75 by pulling on the wire extraction grip 77. The guide tube 75 is then extracted by pulling on the guide tube extraction grip 78. The cannula 79 is removed from the chest and the circumferential attachment cord (not shown in this view), and the lateral attachment cord 80 can be fastened to secure the jacket 71.

The above specification and drawings provide a description of a cardiac reinforcement device and method of using on the heart. Since many embodiments of the invention can be made without departing from the spirit and scope of the invention, the invention resides in the claims hereinafter appended.

What is claimed is:

1. An apparatus for placement on a heart of a patient to treat a heart condition characterized at least in part by diastolic expansion of a size of the heart, the apparatus comprising:
    (a) a jacket comprising flexible open cell material;
        (i) said flexible open cell material being pre-formed in a cone shape with a base and an apex;
            (A) said base defining an opening sized to receive a heart;
        (ii) said jacket for circumferentially surrounding a heart and exerting a variable amount of pressure on the heart as a function of an amount of dilation of the heart, wherein the amount of pressure increases with increasing dilation of the heart;
            (A) said flexible open cell material being sufficiently flexible to move with expansion and contraction of a heart and such that force on one portion of a heart is transmitted circumferentially through the material to another portion of the heart.

2. An apparatus according to claim 1 wherein:
    (a) said material is elastic.

3. An apparatus according to claim 1 wherein:
    (a) said jacket is sized to constrain diastolic expansion beyond a predetermined limit.

4. An apparatus according to claim 1 wherein:
    (a) said material is formed in an open cell construction with a plurality of open cells defined by interconnected, elongated elements.

5. An apparatus according to claim 1 wherein:
    (a) said jacket is sized to be applied to the epicardium of the heart.

6. An apparatus according to claim 1 wherein:
    (a) said jacket is sized to be applied to the pericardium of the heart.

7. An apparatus according to claim 1 wherein:
    (a) said jacket includes a shape memory material.

8. An apparatus according to claim 1 wherein:
    (a) said material is inelastic.

9. An apparatus according to claim 1 wherein:
    (a) said material has a compliance less than a compliance of a wall of the heart.

10. An apparatus for placement on a heart of a patient to treat a heart condition characterized at least in part by diastolic expansion of a size of the heart, the apparatus comprising:
    (a) a jacket comprising flexible open cell material;
        (i) said flexible open cell material being pre-formed in a cone shape with a base and an apex;
            (A) said base defining an opening sized to receive a heart;
            (B) said jacket for surrounding at least a portion of a heart and exerting a variable amount of pressure on the heart as a function of an amount of dilation of the heart, wherein the amount of pressure increases with increasing dilation of the heart; and
            (C) said flexible open cell material comprising an elastic material that moves with expansion and contraction of a heart.

11. An apparatus according to claim 10 wherein:
(a) said jacket is adapted to circumferentially surround a heart; and
(b) said elastic material is sufficiently flexible to move with expansion and contraction of a heart such that force on one portion of a heart is transmitted circumferentially through the jacket to another portion of the heart.

12. An apparatus according to claim 10 wherein:
(a) said jacket is sized to be applied to the epicardium of the heart.

13. An apparatus according to claim 10 wherein:
(a) said jacket is sized to be applied to the pericardium of the heart.

14. An apparatus according to claim 10 wherein:
(a) said jacket includes a shape memory material.

15. An apparatus according to claim 10 wherein:
(a) said flexible open cell material has a compliance lower than a compliance of a wall of the heart.

16. An apparatus according to claim 10 wherein:
(a) said jacket is sized to constrain diastolic expansion beyond a predetermined limit.

* * * * *